(12) United States Patent
Takahashi et al.

(10) Patent No.: US 10,180,410 B2
(45) Date of Patent: Jan. 15, 2019

(54) ULTRASONIC TEST SYSTEM, ULTRASONIC TEST METHOD AND AIRCRAFT STRUCTURAL OBJECT

(71) Applicant: FUJI JUKOGYO KABUSHIKI KAISHA, Tokyo (JP)

(72) Inventors: Kohei Takahashi, Tokyo (JP); Hideki Soejima, Tokyo (JP)

(73) Assignee: SUBARU CORPORATION, Tokyo (JP)

( * ) Notice: Subject to any disclaimer, the term of this patent is extended or adjusted under 35 U.S.C. 154(b) by 224 days.

(21) Appl. No.: 15/175,412

(22) Filed: Jun. 7, 2016

(65) Prior Publication Data

US 2016/0363562 A1 Dec. 15, 2016

(30) Foreign Application Priority Data

Jun. 12, 2015 (JP) ................................. 2015-118956

(51) Int. Cl.
*G01N 29/04* (2006.01)
*G01N 29/24* (2006.01)
(Continued)

(52) U.S. Cl.
CPC ......... *G01N 29/043* (2013.01); *G01N 29/041* (2013.01); *G01N 29/2418* (2013.01);
(Continued)

(58) Field of Classification Search
CPC .... G01N 29/04; G01N 29/041; G01N 29/043; G01N 29/24; G01N 29/2418;
(Continued)

(56) References Cited

U.S. PATENT DOCUMENTS 4,848,159 A * 7/1989 Kennedy ............. G01N 29/265
73/588
5,841,031 A 11/1998 Chung
(Continued)

FOREIGN PATENT DOCUMENTS

JP S61-245055 10/1986
JP H05-133942 5/1993
(Continued)

OTHER PUBLICATIONS

Partial European search report dated Nov. 17, 2016, in Patent Application No. 16 17 3882.8 (9 pages).
(Continued)

*Primary Examiner* — Manish S Shah
*Assistant Examiner* — Suman K Nath
(74) *Attorney, Agent, or Firm* — Smith, Gambrell & Russell, LLP (57) ABSTRACT

According to one implementation, an ultrasonic test system includes at least one ultrasonic transducer, at least one ultrasonic sensor and a damage detection part composed of at least circuitry. The at least one ultrasonic transducer transmits an ultrasonic wave toward at least one test region. The at least one ultrasonic sensor detects the ultrasonic wave which has passed through the at least one test region. The damage detection part is configured to detect whether there is a damage in the at least one test region, based on a difference between a waveform corresponding to the ultrasonic wave detected by the at least one ultrasonic sensor and a reference waveform. The at least one ultrasonic transducer and the at least one ultrasonic sensor are disposed at positions which apart from each other with an interval longer than 300 mm.

13 Claims, 7 Drawing Sheets

(51) Int. Cl.
*G01N 29/44* (2006.01)
*G01N 29/46* (2006.01)

(52) U.S. Cl.
CPC ......... *G01N 29/4436* (2013.01); *G01N 29/46* (2013.01); *G01N 2291/0289* (2013.01); *G01N 2291/044* (2013.01); *G01N 2291/2694* (2013.01)

(58) Field of Classification Search
CPC .... G01N 29/44; G01N 29/4436; G01N 29/46; G01N 2291/0289; G01N 2291/0423; G01N 2291/0427; G01N 2291/044; G01N 2291/102; G01N 2291/103; G01N 2291/105; G01N 2291/106
USPC ......... 73/620, 621, 624, 625, 627, 628, 632, 73/641, 643
See application file for complete search history.

(56) References Cited

U.S. PATENT DOCUMENTS

| | | | |
|---|---|---|---|
| 6,105,431 | A | 8/2000 | Duffill et al. |
| 7,325,456 | B2* | 2/2008 | Kim ................ G01H 9/004 73/587 |
| 8,483,978 | B2 | 7/2013 | Tsubata |
| 8,499,632 | B1 | 8/2013 | Ihn et al. |
| 9,632,062 | B2* | 4/2017 | Tanaka .................. G01N 29/04 |
| 2005/0067559 | A1 | 3/2005 | Ogisu et al. |
| 2007/0167133 | A1 | 7/2007 | Tomlinson, Jr. et al. |
| 2011/0284508 | A1* | 11/2011 | Miura .................. B23K 31/125 219/121.64 |
| 2013/0008253 | A1 | 1/2013 | Tsuda |
| 2014/0330528 | A1 | 11/2014 | Soejima et al. |
| 2015/0096382 | A1* | 4/2015 | Voor, Jr. ............... G01N 29/26 73/633 |

FOREIGN PATENT DOCUMENTS

| | | |
|---|---|---|
| JP | H09-229909 | 9/1997 |
| JP | H11-02353 | 1/1999 |
| JP | 2002-040002 A | 2/2002 |
| JP | 2008-002923 A | 1/2008 |
| JP | 2011-185921 | 9/2011 |
| JP | 2011-191230 A | 9/2011 |
| JP | 2014-194379 | 10/2014 |

OTHER PUBLICATIONS

Sun, K J et al., Feasibility of using lamb waves for corrosion detection in layered aluminum aircraft structures, Proceedings of Theultrasonics Symposium, US, IEEE, Oct. 31, 1993, vol. 2, p. 733-736.

Gachagan, A et al., Generation and reception of ultrasonic guided waves in composite plates using conformable piezoelectric transmitters and optical-fiber detectors, IEEE Transactions on Ultrasonics, Ferroelectrics and Frequency Control, US, IEEE, Jan. 1, 1999, vol. 46, No. 1, pp. 72-81.

Okabe, Y et al., Evaluation of debonding progress in composite bonded structures using ultrasonic waves received in fiber Bragg grating sensors, Smart Materials and Structures, GB, IOP Publishing LTD., Aug. 1, 2007, vol. 16, No. 4, pp. 1370-1378.

Staszewski, W J et al., Wavelet signal processing for enhanced lamb-wave defect detection in composite plates using optical fiber detection, Optical Engineering, Soc. of Photo-Optical Instrumentation Engineers, Jul. 1, 1997,vol. 36, No. 7, pp. 1877-1888.

First Japanese Office Action dated Mar. 14, 2017, in Japanese Patent Application No. 2015-118956 (11 pages—Japanese with English machine translation).

Soejima et al. Development of Structural Health Monitoring Technology Using Lamb Waves. Subaru Technical Review, Japan, Jun. 2011, No. 38, pp. 150-156 (English abstract).

Japanese Notification of Reasons for Refusal dated Sep. 26, 2017, in Japanese Patent Application No. 2015-118956 (8 pages—Japanese with English translation).

Extended European search report dated Feb. 17, 2017, in European Patent Application No. 16 17 3882.8 (12 pages).

* cited by examiner

ULTRASONIC TEST SYSTEM, ULTRASONIC TEST METHOD AND AIRCRAFT STRUCTURAL OBJECT

CROSS REFERENCES TO RELATED APPLICATIONS

This application is based upon and claims the benefit of priority from Japanese Patent Application No. 2015-118956, filed on Jun. 12, 2015; the entire contents of which are incorporated herein by reference.

FIELD

Implementations described herein relate generally to an ultrasonic test system, an ultrasonic test method, and an aircraft structural object.

BACKGROUND

Conventionally, an ultrasonic flaw inspection method is known as a method of nondestructively inspecting a structural member of an aircraft or the like. As a specific example, a damage length measurement system which can measure a length of damage, such as delamination or peeling, in an adhesive part or a bonded part, using an actuator which emits ultrasonic waves toward a region to be inspected and an FBG (fiber Bragg grating) sensor for receiving ultrasonic reflected waves reflected in the region to be inspected has been proposed (for example, refer to Japanese Patent Application Publication JP 2011-185921 A and Japanese Patent Application Publication JP 2014-194379 A).

Although a length and a size of damage in a range to be inspected can be measured by the conventional ultrasonic test method, only a local range, such as a bonded part, can be inspected. That is, only damage in a short distance from an actuator and a sensor can be detected. Specifically, an actuator and a sensor require to be disposed with an interval of not more than 300 mm at most. Therefore, an inspection of a large aircraft part or the like requires to dispose a large number of actuators and sensors with a high density, and that is not realistic.

Accordingly, an object of the present invention is to enable to nondestructively detect a damage in an object to be tested with targeting a wider range.

SUMMARY OF THE INVENTION

In general, according to one implementation, an ultrasonic test system includes at least one ultrasonic transducer, at least one ultrasonic sensor and a damage detection part composed of at least circuitry. The at least one ultrasonic transducer transmits an ultrasonic wave toward at least one test region. The at least one ultrasonic sensor detects the ultrasonic wave which has passed through the at least one test region. The damage detection part is configured to detect whether there is a damage in the at least one test region, based on a difference between a waveform corresponding to the ultrasonic wave detected by the at least one ultrasonic sensor and a reference waveform. The at least one ultrasonic transducer and the at least one ultrasonic sensor are disposed at positions which apart from each other with an interval longer than 300 mm.

Further, according to one implementation, an aircraft structural object to which the above-mentioned ultrasonic test system has been attached is provided.

Further, according to one implementation, an ultrasonic test method includes: transmitting an ultrasonic wave toward a test region by at least one ultrasonic transducer; detecting the ultrasonic wave, having passed through the test region, by at least one ultrasonic sensor disposed at a position apart from the at least one ultrasonic transducer with an interval longer than 300 mm; and detecting whether there is a damage in the test region, based on a difference between a waveform corresponding to the ultrasonic wave detected by the at least one ultrasonic sensor and a reference waveform.

Further, according to one implementation, an ultrasonic test method includes: transmitting an ultrasonic wave toward a test region by at least one ultrasonic transducer; detecting the ultrasonic wave, having passed through the test region, by at least one ultrasonic sensor; detecting whether there is a damage in the test region, based on a difference between a waveform corresponding to the ultrasonic wave detected by the at least one ultrasonic sensor and a reference waveform; and setting a new test region and performing a nondestructive test of the damage in the new test region when the damage has been detected in the test region. The new test region is set to include the damage and be narrower than the test region.

DETAILED DESCRIPTION

An ultrasonic test system, an ultrasonic test method and an aircraft structural object according to implementations of the present invention will be described with reference to the accompanying drawings.

(Configuration and Function)

Figure 1:
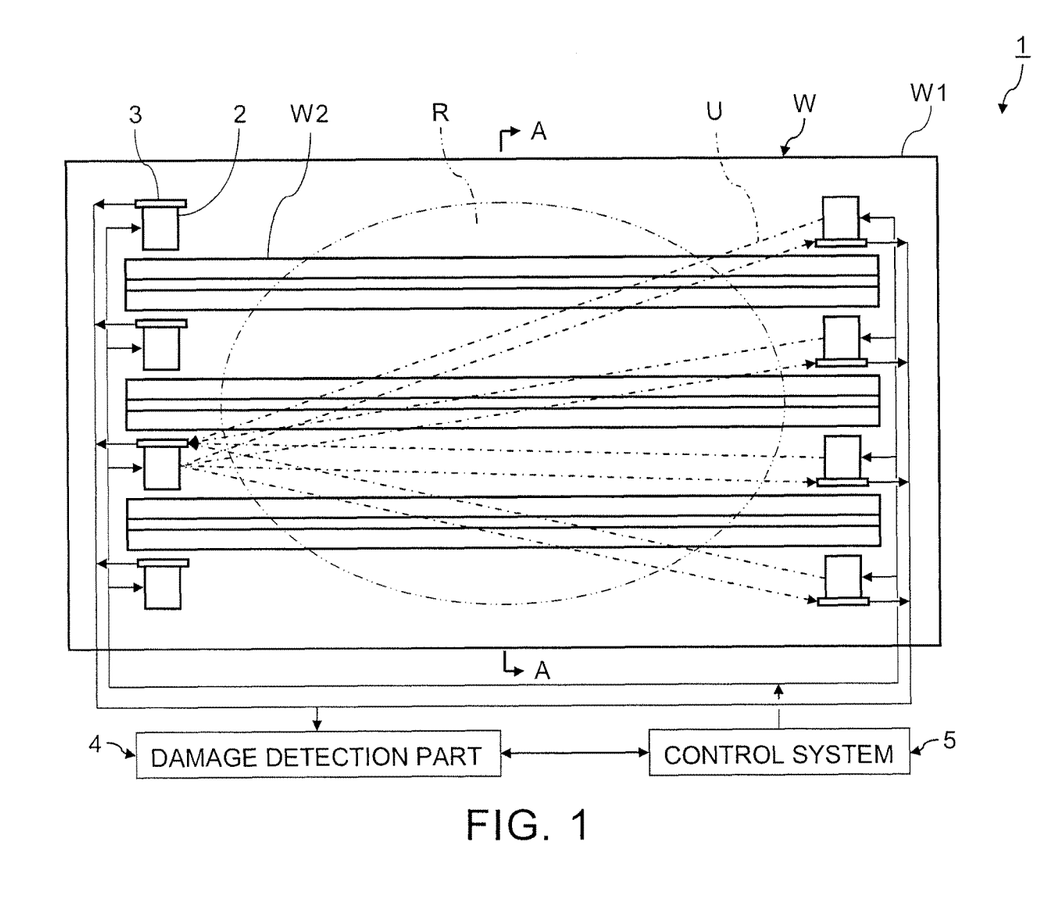
FIG. 1 shows a structure of an ultrasonic test system according to an implementation of the present invention.
Figure 2:
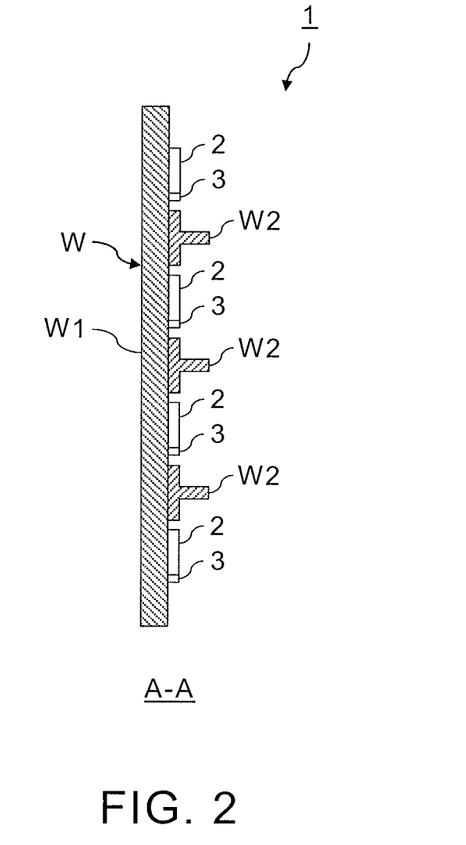
FIG. 2 is a sectional view at the position A-A of the ultrasonic test system shown in FIG. 1.

FIG. 1 shows a structure of an ultrasonic test system according to an implementation of the present invention, and FIG. 2 is a sectional view at the position A-A of the ultrasonic test system shown in FIG. 1.

An ultrasonic test system 1 is a system which nondestructively detects whether a test region R of an object W to be tested has a damage using ultrasonic waves U which have transmitted the test region R. For that purpose, the ultrasonic test system 1 has at least one ultrasonic transducer 2 which transmits an ultrasonic wave U to a test region R, at least one ultrasonic sensor 3 which detects an ultrasonic wave U which has passed the test region R, a damage detection part 4, and a control system 5.

In particular, when an object W to be tested is a large part, such an aircraft structural object, a size of test region R becomes wide. For this reason, at least one ultrasonic transducer 2 and at least one ultrasonic sensor 3 can be disposed at positions which apart from each other with an interval longer than 300 mm. Thereby, a nondestructive test of a test region R which has a width longer than 300 mm can be performed. In particular, setting appropriate conditions as described later makes it possible to dispose at least one ultrasonic transducer 2 and at least one ultrasonic sensor 3 at positions which apart from each other with an interval of not less than 1000 mm. In that case, a nondestructive test of a test region R which has a width of not less than 1000 mm can be performed.

From a viewpoint of widening a test region R two-dimensionally, it is preferable to dispose plural ultrasonic transducers 2 which transmit ultrasonic waves U to a test region R from different positions respectively. In this case, respective ultrasonic waves U from the ultrasonic transducers 2 which have passed the test region R are to be detected by at least one ultrasonic sensor 3. It is also effective to dispose plural ultrasonic sensors 3 from a viewpoint of widening a test region R two-dimensionally.

Specifically, when the ultrasonic transducers 2 are disposed at different positions to transmit ultrasonic waves U, a test region R can be widened in an array direction of the ultrasonic transducers 2. Meanwhile, when the ultrasonic sensors 3 are disposed at different positions to receive ultrasonic waves U, a test region R can be widened in an array direction of the ultrasonic sensors 3. Therefore, a test region R can become a wider range by disposing plural ultrasonic transducers 2 and plural ultrasonic sensors 3. In particular, when plural inspection units each consisting of the ultrasonic transducer 2 and the ultrasonic sensor 3 are disposed at different positions, it becomes possible to diagnose the existence of damage in a test region R by mutually transmitting and receiving ultrasonic waves U from and to the inspection units.

It becomes possible to perform an effective inspection by disposing at least one ultrasonic transducer 2 and at least one ultrasonic sensor 3 at appropriate positions according to a structure of an object W to be tested. As an example, when an object W to be tested has a structure in which at least one elongated structure W2 is attached on a plate-like part W1, it is preferable to dispose plural ultrasonic transducers 2 and plural ultrasonic sensors 3, and to dispose at least one pair of the ultrasonic transducer 2 and the ultrasonic sensor 3 in each of the both sides of the at least one elongated structure W2.

In this case, even when an ultrasonic wave U attenuates caused by reflecting on the elongated structure W2, it becomes possible to accurately and certainly detect the existence of damage in each of the both sides of area which is segmented with the elongated structure W2. That is, even when an ultrasonic wave U with a sufficient intensity cannot pass the elongated structure W2, the existence of damage in the both sides of the elongated structure W2 is detectable. In particular, when a lot of elongated structures W2 are formed on a plate-like part W1, an intensity of ultrasonic wave U which passes all the elongated structures W2 may attenuate, and therefore, it may become difficult to detect the ultrasonic wave U with a sufficient signal-to-noise ratio (SNR). Accordingly, when a lot of elongated structures W2 are attached on a plate-like part W1, it is effective to dispose at least a pair of the ultrasonic transducer 2 and the ultrasonic sensor 3 in each of the both sides of each elongated structure W2.

Note that, as a result of transmitting and receiving ultrasonic waves U to and from an object W to be tested having three elongated structures W2 on a plate-like part W1 of which size is about 1 m×1 m, it was confirmed that an ultrasonic wave U which had transmitted the three elongated structures W2 could be detected by the ultrasonic sensor 3 with a sufficient SNR as long as appropriate conditions were determined so that a detection sensitivity of ultrasonic waves U would become satisfactory. Therefore, when not less than four elongated structures W2 are attached on a plate-like part W1, it is considered to be preferable to dispose an appropriate number of the ultrasonic transducers 2 and the ultrasonic sensors 3 at appropriate positions so that each ultrasonic wave U which has passes not more than three elongated structures W2 can be detected by a single ultrasonic sensor 3 or plural ultrasonic sensors 3, from a viewpoint of avoiding unnecessary signal processing.

Furthermore, when at least a pair of the ultrasonic transducer 2 and the ultrasonic sensor 3 was disposed between two adjacent elongated structures W2 and an ultrasonic wave U was transmitted from the ultrasonic transducer 2, it was confirmed that an attenuation amount of the ultrasonic wave U could be reduced since the ultrasonic wave U propagated toward the ultrasonic sensor 3 with reflecting on the two adjacent elongated structures W2. Accordingly, when an ultrasonic wave U is transmit and received to and from an object W to be tested of which structure has plural elongated structures W2 on a plate-like part W1, it is effective to dispose at least a pair of the ultrasonic transducer 2 and the ultrasonic sensor 3 between at least two adjacent elongated structures W2, from a viewpoint of detecting damage with a high precision.

In the illustrated example, eight ultrasonic transducers 2 and eight ultrasonic sensors 3 have been disposed on an object W to be tested of which structure has three elongated structures W2 on a plate-like part W1. Then, two pairs of the ultrasonic transducers 2 and the ultrasonic sensors 3 have been disposed oppositely in each of the both sides of each elongated structure W2. In other words, two sets of the ultrasonic transducers 2 and the ultrasonic sensors 3 have been disposed oppositely in each of the areas divided with the respective elongated structures W2. Therefore, in each area segmented with the elongated structures W2, it is possible to transmit ultrasonic waves U bidirectionally. Moreover, an ultrasonic wave U which has passed elongated structures W2 is detectable in a sufficient SNR when the number of the elongated structures W2 is about three as described above. Therefore, ultrasonic waves U can be transmitted to a test region R in a meshed pattern. Consequently, the existence of damage in the four areas of the plate-like part W1 divided by the elongated structures W2 can be detected with a high precision, respectively.

As an example of object W to be tested which has such a structure, an aircraft structural object having at least one of spars, ribs, and stringers attached on a panel (it is also called a skin) is mentioned. Therefore, a nondestructive test which uses ultrasonic waves U can be performed for a meter class large-sized aircraft structural object.

Whether there is damage can be determined based on change of a waveform of at least one ultrasonic wave U which has passed a test region R. Specifically, when damage exists on a propagation pathway of an ultrasonic wave U, the waveform of the ultrasonic wave U changes. Therefore, whether damage exists in a test region R can be determined by taking advantage of a difference between a waveform of ultrasonic wave U in a case that no damage exists on the propagation pathway of the ultrasonic wave U and one in a case that damage exists on the propagation pathway of the ultrasonic wave U. More specifically, when an amount in difference of a waveform, corresponding to an ultrasonic wave U detected by the ultrasonic sensor 3, from a reference waveform is large, it can be judged that damage exists on the propagation pathway of the ultrasonic wave U.

Therefore, it is important to detect change in a waveform of an ultrasonic wave U in sufficient accuracy even when a distance between the ultrasonic transducer 2 and the ultrasonic sensor 3 is long. As a result of examinations, it was confirmed that when an ultrasonic wave U of which a frequency band was not less than 50 kHz and not more than 500 kHz was transmitted to a test region R in which damage existed, the waveform of the ultrasonic wave U which had passed the damaged portion changed to such an extent that the change could be observed. In particular, it was confirmed that when an ultrasonic wave U of which a frequency band was not less than 50 kHz and not more than 150 kHz was transmitted to a test region R in which damage existed, the attenuation of the ultrasonic wave U was small and that a waveform change of the ultrasonic wave U which had passed the damaged portion was also detectable with a practical SNR and practical accuracy. This result can be considered to be common regardless of whether the material which propagates an ultrasonic wave U is metal or a composite material.

Therefore, it is appropriate that an ultrasonic wave U of which frequency is not less than 50 kHz and not more than 500 kHz is transmitted from each ultrasonic transducer 2. In particular, it is preferable that an ultrasonic wave U of which frequency is not less than 50 kHz and not more than 150 kHz is transmitted from each ultrasonic transducer 2 from a viewpoint of detecting the existence of damage in a test region R with much higher precision.

Moreover, when ultrasonic waves U transmitted from plural ultrasonic transducers 2 are received by a common ultrasonic sensor 3 and, on the contrary, when an ultrasonic wave U transmitted from a single ultrasonic transducer 2 is received by plural ultrasonic sensors 3, it is important that each ultrasonic wave U propagates an object W to be tested with spreading enough. Meanwhile, when an ultrasonic wave U is a non-directional spherical wave, an ultrasonic reflected wave from an unintended direction and noise may be received by an ultrasonic sensor 3. Therefore, it is important to transmit an ultrasonic wave U which has a directivity to an appropriate extent, from a viewpoint of allowing an ultrasonic wave U, transmitted from an ultrasonic transducer 2 which does not oppose to an ultrasonic sensor 3, to be received by the ultrasonic sensor 3, with securing an SNR and accuracy.

Moreover, it is effective to use a Lamb wave from a viewpoint of improving an SNR and accuracy of an ultrasonic wave U which is received by an ultrasonic sensor 3. That is, it is preferable to transmit a Lamb wave as an ultrasonic wave U from each ultrasonic transducer 2. A Lamb wave is a wave which propagates a thin plate, of which thickness is not more than half of a wavelength of the ultrasonic wave U, in an in-plane direction, and also is a wave in which a symmetric mode and an asymmetric mode are mixed.

As an ultrasonic transducer 2 for transmitting an ultrasonic wave U, a piezoelectric element, such as lead zirconate titanate (PZT), can be used. Meanwhile, as an ultrasonic sensor 3 for detecting an ultrasonic wave U, an ultrasonic transducer, such as a piezoelectric element, or a sensor, such as an optical fiber sensor, can be used.

In case of using an ultrasonic transducer as an ultrasonic sensor 3, an ultrasonic signal is converted into an electric signal in the ultrasonic transducer. Meanwhile, in case of using an optical fiber sensor as an ultrasonic sensor 3, an ultrasonic signal is converted into an optical signal in the optical fiber sensor. Specifically, when a minute strain arises in an optical fiber sensor due to a vibration by an ultrasonic wave U, an optical characteristic of the optical fiber sensor changes according to an amount of the strain. As a result, an optical signal which has an amplitude according to an amplitude of the ultrasonic signal can be output from the optical fiber sensor.

Note that, when an ultrasonic transducer is used as an ultrasonic sensor 3, in the case that an ultrasonic wave U having a frequency which shifts greatly from a resonance frequency is transmitted, it may become impossible to receive the ultrasonic wave U with a sufficient sensitivity. On the other hand, an optical fiber sensor is an ultrasonic sensor 3 which has no frequency dependency in sensitivity. Therefore, when an optical fiber sensor is used as an ultrasonic sensor 3, it becomes possible to detect a more broadband ultrasonic wave U with high sensitivity, compared with a case of using an ultrasonic transducer as an ultrasonic sensor 3.

Moreover, an optical fiber sensor has receiving directivity. Therefore, when an optical fiber sensor is used as an ultrasonic sensor 3, it becomes possible to avoid detecting ultrasonic waves U which propagate from unnecessary directions, thereby a necessary ultrasonic signal can be detected selectively.

Therefore, it is a preferable condition to use an optical fiber sensor as each ultrasonic sensor 3. When an optical fiber sensor which has a receiving directivity is used as an ultrasonic sensor 3, it is required to dispose an ultrasonic transducer 2 and the optical fiber sensor so as to overlap a propagated area of ultrasonic wave U which is transmitted from the ultrasonic transducer 2 with an area in which an ultrasonic wave U can be detected by the optical fiber sensor.

As an example of an optical fiber sensor, an FBG sensor and a phase-shifted FBG (PS-FBG) sensor are mentioned. A PS-FBG is an FBG in which a local phase shift is introduced into a periodic change of a refractive index.

As described above, when Lamb waves, each having a directivity, each propagating in a fan shape, and each having a frequency not less than 50 kHz and not more than 150 kHz are transmitted to a test region R from plural directions, and when the Lamb waves which passed through the test region R are detected by fiber sensors, a very wide range can be inspected.

An ultrasonic wave U which was detected by an ultrasonic sensor 3 is converted into an electric signal when the ultrasonic sensor 3 is an ultrasonic transducer. Meanwhile, when the ultrasonic sensor 3 is an optical fiber sensor, an ultrasonic wave U is converted into an optical signal. Then, the converted signal is output to the damage detection part 4. Hereinafter, an example case that each ultrasonic sensor 3 is an optical fiber sensor will be described.

The damage detection part 4 is an element to detect the existence of a damage in a test region R based on an amount of difference between a waveform corresponding to an ultrasonic wave U detected by an ultrasonic sensor 3 and a reference waveform. The damage detection part 4 also can be provided with various signal processing functions so that change of a waveform of an ultrasonic wave U can be detected in a sufficient accuracy even when a test region R is large as in a case of disposing an ultrasonic transducer 2 and an ultrasonic sensor 3 at positions away from each other with a distance of over 300 mm. In particular, when appropriate signal processing is performed to an ultrasonic wave U which was detected by an ultrasonic sensor 3, it becomes possible to detect a change of a waveform of the ultrasonic wave U even when an ultrasonic transducer 2 and the ultrasonic sensor 3 are disposed at positions away from each other with a distance not less than 1000 mm.

Figure 3:
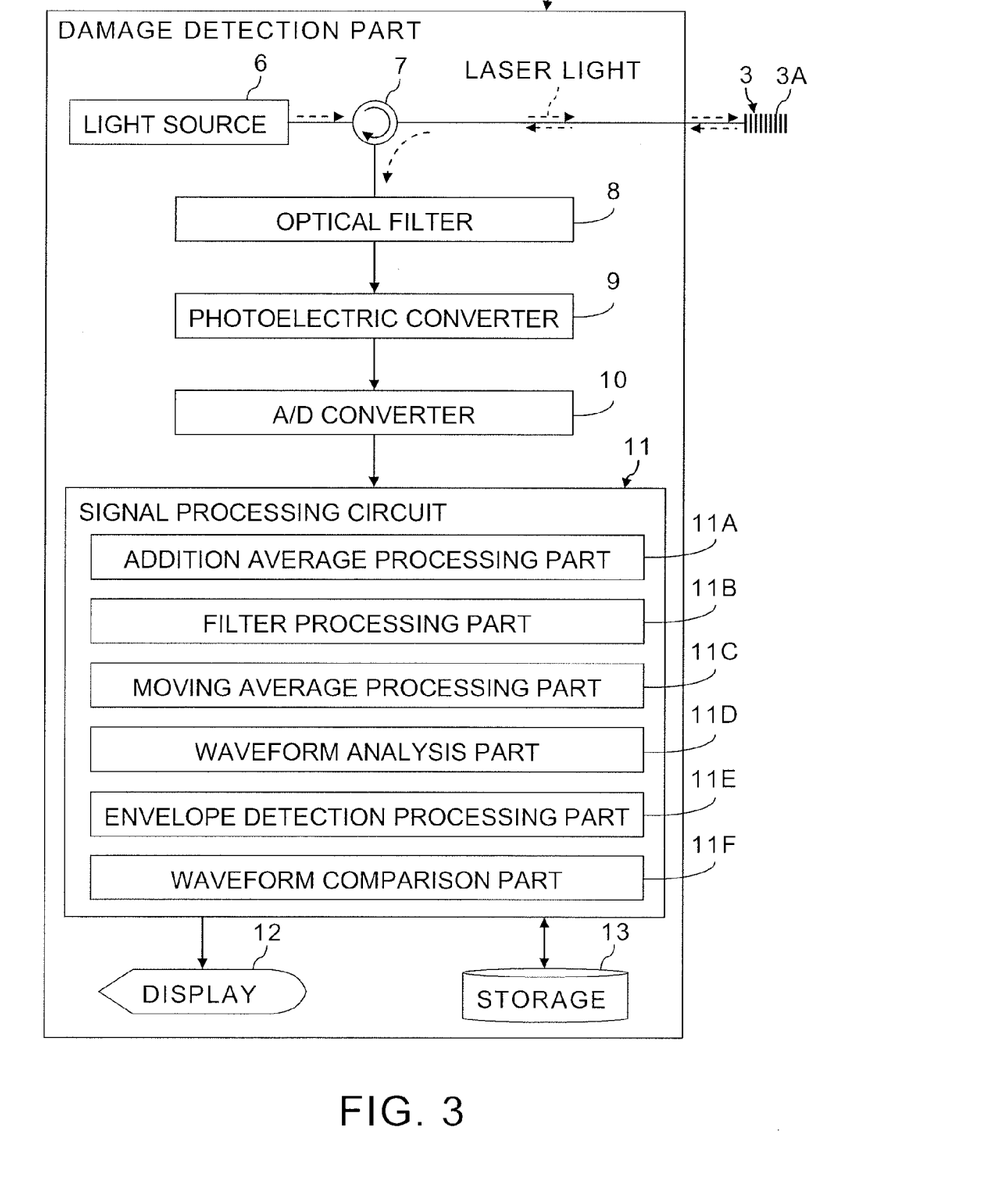
FIG. 3 is a functional block diagram showing an example of detailed configuration of the damage detection part shown in FIG. 1.

FIG. 3 is a functional block diagram showing an example of detailed configuration of the damage detection part 4 shown in FIG. 1.

The damage detection part 4 can be composed of a light source 6, an optical circulator 7, an optical filter 8, a photoelectric converter 9, an A/D (analog to digital) converter 10, a signal processing circuit 11, a display 12, and a storage 13. The signal processing circuit 11 functions as an addition average processing part 11A, a filter processing part 11B, a moving average processing part 11C, a Fourier transform (FT) part 11D, an envelope detection processing part 11E and a waveform comparison part 11F by executing computer program. The program which is executed by the signal processing circuit 11 may be stored in the storage 13 so that the signal processing circuit 11 can read and execute the program. Alternatively, the program may be stored in the signal processing circuit 11 itself.

A laser light which was emitted from the light source 6 enters an FBG sensor 3A, as an example of optical fiber sensor, through the optical circulator 7. The light which was reflected on the FBG sensor 3A enters the optical filter 8 through the optical circulator 7. The reflected light which transmitted the optical filter 8 is output to the photoelectric converter 9.

When an ultrasonic wave U propagates in the FBG sensor 3A, a minute strain arises in the FBG sensor 3A. Therefore, a light reflection characteristic of the FBG sensor 3A changes according to a strain amount. Accordingly, a wavelength distribution of a reflected light from the FBG sensor 3A changes according to an amplitude of vibration of an ultrasonic wave U. Thereby, vibration of intensity of an ultrasonic wave U is converted into a vibration of a wavelength of an optical signal. An optical signal which was acquired in the FBG sensor 3A is output to the photoelectric converter 9 through the optical filter 8.

The optical filter 8 can be prepared when required. The optical filter 8 is an optical element which limits a wavelength band of an optical signal. As an example of an optical element used as the optical filter 8, an arrayed waveguide grating (AWG), an FBG or a PS-FBG are mentioned.

Figure 4:
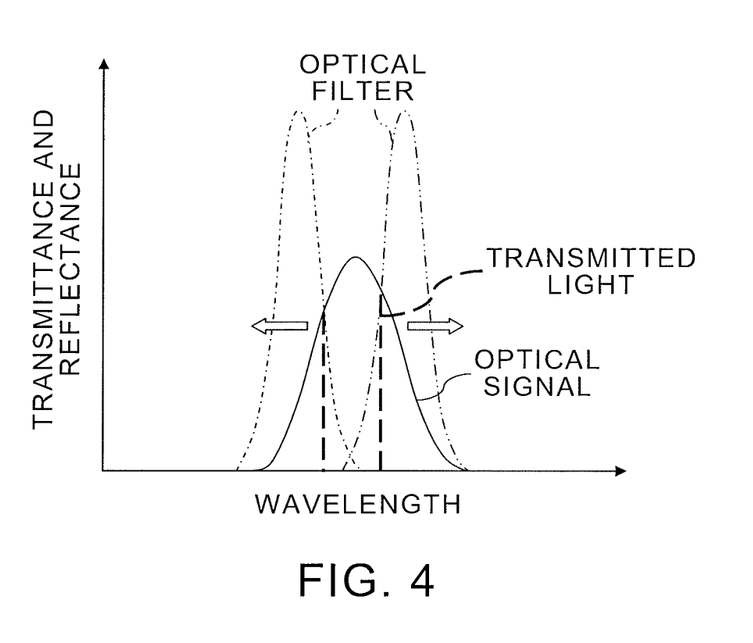
FIG. 4 shows a graph for explaining the principle in which the optical filter shown in FIG. 3 amplifies an amplitude of an optical signal.

FIG. 4 shows a graph for explaining the principle in which the optical filter 8 shown in FIG. 3 amplifies an amplitude of an optical signal.

In FIG. 4, the horizontal axis shows a wavelength of light, and the vertical axis shows a reflectance of light in the FBG sensor 3A and a transmittance of light in an AWG used as the optical filter 8. Moreover, in FIG. 4, the solid line shows the reflectance of light in the FBG sensor 3A, and the dotted lines show the transmittance of light in the AWG.

A wavelength spectrum of an optical signal which is output from the FBG sensor 3A becomes a spectrum, which is exemplified as the solid line in FIG. 4, corresponding to the reflectance of light in the FBG sensor 3A. Then, an optical signal which is output from the FBG sensor 3A becomes an optical signal in which wavelengths of the wavelength spectrum exemplified as the solid line in FIG. 4 vibrate, as described above.

Meanwhile, the light transmission characteristic of the AWG is adjusted to a characteristic which is exemplified by the dotted lines in FIG. 4. Specifically, the light reflectance in the FBG sensor 3A and the light transmittance in the AWG are determined so that a wavelength spectrum of an optical signal which is output from the FBG sensor 3A partially overlaps with the light transmittance in the AWG.

Then, an intensity of an optical signal which transmits the AWG is to change according to wavelengths of the optical signal which enters the AWG. As a result, an optical signal in which a wavelength vibrates can be converted into an optical signal in which the intensity vibrates. The light transmittance in the AWG is set so that two peaks respectively appear in the both sides of a peak of the light reflectance in the FBG sensor 3A, as exemplified in FIG. 4. Therefore, a transmitted light from the AWG becomes into a light which has two components whose wavelengths are different from each other. Moreover, the two components have a relation that the intensity of one component becomes larger when the intensity of the other component becomes smaller. Therefore, when a difference between the two components which are contained in a transmitted light from the AWG is used as an optical signal which is output from the AWG, an optical signal in which the intensity vibrates and the amplitude is amplified can be acquired.

Note that, an FBG or a PS-FBG may also be used as the optical filter 8. In that case, what is necessary is to overlap a light transmittance in the FBG sensor 3A with a light transmittance in an FBG or a PS-FBG. In particular, a PS-FBG shows a highly sharp peak in each of a light transmittance and a light reflectance. Therefore, when a PS-FBG is used as the optical filter 8, an amplitude of an optical signal can be amplified more.

Moreover, although a reflected light from the FBG sensor 3A is used as an optical signal in an example shown in FIG. 3, a transmitted light from the FBG sensor 3A may also be used as an optical signal. Meanwhile, as for the optical filter 8, not only a transmitted light but a reflected light can be used as an output signal. Therefore, optical characteristics of the FBG sensor 3A and the optical filter 8 are determined so that an amplitude of an optical signal which is output from the optical filter 8 is amplified.

Thus, when the optical filter 8 is installed in the output of the FBG sensor 3A, an optical signal in which wavelengths change according to a vibration of intensity of ultrasonic wave U can be converted into an optical signal in which light intensity changes according to the vibration of the intensity of the ultrasonic wave U. Moreover, an amount of change in light intensity of an optical signal can be larger than an amount of change in wavelength. That is, an amount of change in vibration of an optical signal can be amplified substantially. As a result, it becomes possible to detect an optical signal with extremely high sensitivity.

Therefore, it is preferable to install the optical filter 8, which converts an ultrasonic detection signal output as a vibration in light wavelength from the FBG sensor 3A into an ultrasonic detection signal by a vibration in light intensity having a larger amplitude, in the output side of the FBG sensor 3A, from a viewpoint of detecting an ultrasonic wave U with higher sensitivity.

In the photoelectric converter 9, an optical signal which was output from the FBG sensor 3A through the optical filter 8 is converted into an analog electric signal. The analog electric signal generated in the photoelectric converter 9 is converted into a digital electric signal in the A/D converter 10, and subsequently the digital electric signal is output to the signal processing circuit 11.

The addition average processing unit 11A has a function to perform addition averaging processing of an ultrasonic signal which was converted into an electric signal. When addition averaging processing is performed, transmission and detection of an ultrasonic wave U are repeated required times. Then, the ultrasonic signals which were detected over plural times are added to each other. Thereby, random noises which are superimposed on ultrasonic signals can be reduced.

Note that, addition averaging processing may be performed to an analog ultrasonic signal before the A/D conversion. In that case, a processing circuit of analog signal for performing addition averaging processing is installed as the addition average processing part 11A in the former stage of the A/D converter 10.

The filter processing part 11B has a function to perform filter processing of an ultrasonic signal, using an LPF (Low Pass Filter), a HPF (High Pass Filter) or the like. This filter processing can remove noises superimposed in a specific frequency band.

The moving averaging processing part 11C has a function to perform moving averaging processing of an ultrasonic signal. The moving averaging processing is processing which replaces a value of a piece of data to be processed with an average value of n pieces of data just before the piece of data to be processed. The moving averaging processing which obtains an average value without weighting is called a Simple Moving Averaging (SMA) processing. When moving averaging processing, such as simple moving averaging processing, is performed to an ultrasonic signal, smoothing of a waveform of the ultrasonic signal can be performed. Therefore, periodic noises superimposed on an ultrasonic signal can be reduced.

When a value of the number n of pieces of data which is a parameter of moving averaging processing is made small, degradation in sharpness of an ultrasonic signal is reduced while a reduction effect of noises decreases. On the contrary, when a value of the number n of pieces of data is made large, sharpness of an ultrasonic signal decreases while a reduction effect of noises improves.

Therefore, an appropriate value of the number n of pieces of data can be determined experientially by an examination or the like. Alternatively, when moving averaging processing is performed, a value of the number n of pieces of data may be set variably by a manual operation. In that case, a scroll bar for a variable setup of a value of the number n of pieces of data may be displayed on the display 12 as a UI (user interface). Thereby, it becomes possible to detect a change in waveform of an ultrasonic signal with higher sensitivity.

Note that, smoothing processing other than moving averaging processing may be performed to a waveform of an ultrasonic signal corresponding to an ultrasonic wave U which was detected by the ultrasonic sensor 3.

When at least one of such addition averaging processing, filter processing, and smoothing processing is performed as noise removing processing, an SNR can be improved. In particular, it was confirmed that performing at least addition averaging processing and moving averaging processing of an ultrasonic signal amplified by the AWG as the optical filter 8 made it possible to detect a change in amplitude of a Lamb wave with a sufficient SNR even when the ultrasonic transducer 2 and the ultrasonic sensor 3 were disposed at positions away from each other by the distance not less than 1000 mm.

The waveform analysis part 11D has a function to obtain signal waveforms corresponding to plural frequency bands by frequency analysis processing, such as Fourier transform or wavelet transform, of an ultrasonic signal. When signal waveforms corresponding to frequency bands are obtained, it becomes possible to detect a change in waveform with targeting simpler waveforms. Moreover, a change in waveform can be detected with targeting a specific frequency band. Therefore, a detection sensitivity in the existence of damage can be improved further.

The envelope detection processing part 11E has a function to perform envelope detection processing of an ultrasonic signal. When an envelope detection is performed, an accuracy in analyzing a waveform can be improved.

The above mentioned various signal processing can be selected voluntarily to be performed according to a required detection sensitivity of damage. The order of various signal processing can be also determined voluntarily to a theoretical and practical extent. As a typical example, signal processing can be performed in the order of addition averaging processing, filter processing, moving averaging processing, frequency analysis processing such as Fourier transform or wavelet transform, and envelope detection processing.

The waveform comparison part 11F has a function to determine whether damage exists in a test region R by comparing a reference waveform, which is obtained beforehand as a waveform in the case where no damage has arisen in the test region R, with a waveform corresponding to an ultrasonic wave U which was detected by the ultrasonic sensor 3. Note that, a reference waveform and a waveform corresponding to an ultrasonic wave U which was detected by the ultrasonic sensor 3 may be displayed on the display 12 respectively by the waveform comparison part 11F so that a user can visually determine whether damage exists in a test region R.

When the above mentioned signal processing is performed to an ultrasonic signal corresponding to an ultrasonic wave U which was detected by the ultrasonic sensor 3, it is preferable to give also the same signal processing to a reference waveform of ultrasonic signal in the case where damage does not exist in a test region R, from a viewpoint of detecting a change in waveform, in the case where damage exists, with high precision.

Figure 5A:
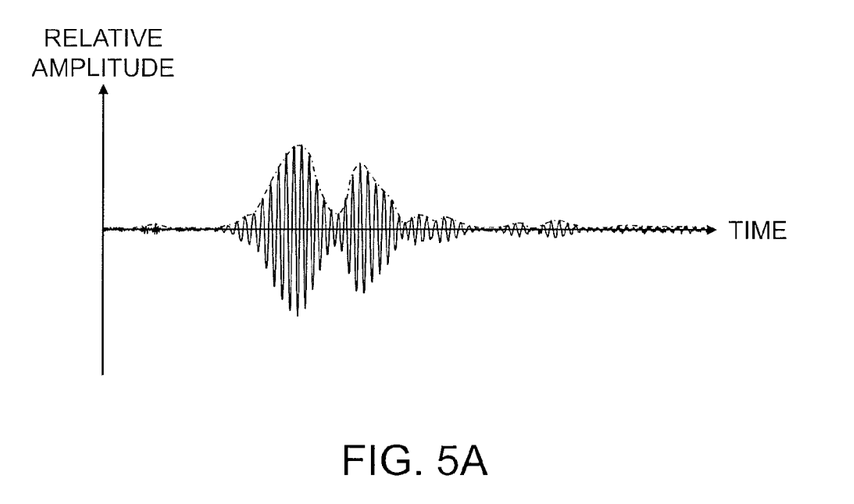
FIGS. 5A and 5B show graphs showing an example of waveforms of ultrasonic signals to be compared in the damage detection part shown in FIG. 1.
Figure 5B:
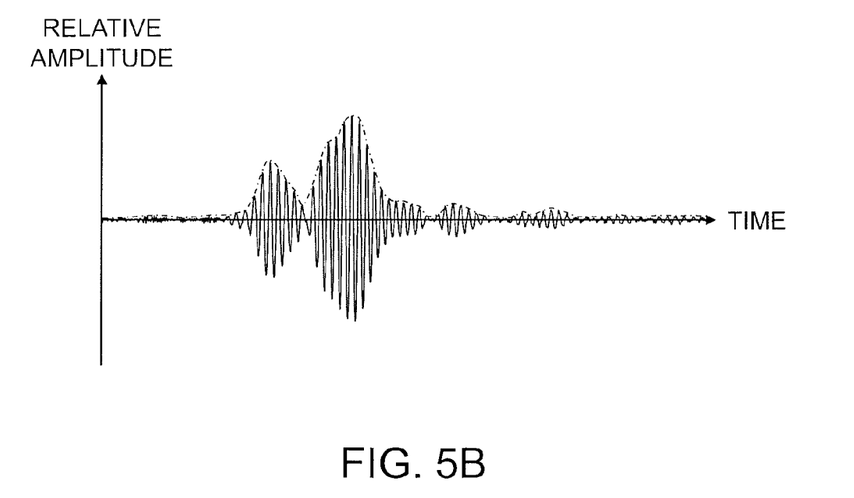

FIGS. 5A and 5B show graphs showing an example of waveforms of ultrasonic signals to be compared in the damage detection part 4 shown in FIG. 1.

In FIGS. 5A and 5B, each vertical axis shows a relative amplitude (relative intensity) of an ultrasonic signal which is detected by the ultrasonic sensor 3, and each horizontal axis shows elapsed time from transmission timing of the ultrasonic wave U. FIG. 5A shows a waveform of an ultrasonic signal including an ultrasonic wave U which was detected by the ultrasonic sensor 3 from a test region R having no damage while FIG. 5B shows a waveform of an ultrasonic signal including an ultrasonic wave U which was detected by the ultrasonic sensor 3 from a test region R having damage. In FIGS. 5A and 5B, each solid line shows an ultrasonic signal acquired by addition averaging processing and moving averaging processing, and each dashed-dotted line shows an envelope curve of the ultrasonic signal which is acquired by an envelope detection of the ultrasonic signal acquired by the addition averaging processing and the moving averaging processing. Note that, when other signal processing is performed, a waveform according to the signal processing is obtained.

As shown in FIGS. 5A and 5B, the waveform of the ultrasonic wave U which transmitted the test region R changes depending on whether damage has arisen in the test region R. Accordingly, a waveform of an ultrasonic signal can be acquired beforehand from the test region R in the state where damage does not exist. A waveform of ultrasonic wave corresponding to the test region R without damage can be stored in the storage 13 as a reference waveform.

Then, it becomes possible to detect the existence of damage in the test region R based on change, from the reference waveform, of a waveform of an ultrasonic signal in the case where damage has arisen. The degree of change, from the reference wave, of a waveform of an ultrasonic signal in the case where damage has arisen can be expressed using an index such as a cross correlation coefficient, a square error or the like. It is practical to compare envelope curves as waveform comparison in view of accuracy.

Note that, a portion corresponding to an ultrasonic wave U may be a part of the ultrasonic signal. For that reason, a time range of a portion corresponding to an ultrasonic wave U may be specified based on a distance between the ultrasonic transducer 2 and the ultrasonic sensor 3, transmission timing of an ultrasonic wave U, and an acoustic velocity so that the specified portion can be extracted for waveform comparison. This is the same as for various signal processing. That is, a portion corresponding to a received ultrasonic wave U may be extracted from an ultrasonic signal. Then, the extracted portion can be subjected to signal processing, such as addition averaging processing.

When an index showing the amount of change, from the reference wave, of a waveform of an ultrasonic signal in the case where damage has arisen is obtained, the existence of the damage can be automatically determined by threshold processing of the index. Specifically, when the amount of change in waveform is not less than a threshold value or more than the threshold value, it can be determined that damage exists in a test region R. Therefore, such operation function can be given to the waveform comparison part 11F so that the waveform comparison part 11F can automatically detect a damage in a test region R.

When ultrasonic waves U are transmitted sequentially from plural ultrasonic transducers 2 disposed on different positions, the ultrasonic waves U are received sequentially by a single ultrasonic sensor 3 or plural ultrasonic sensors 3. In this case, signal processing is sequentially performed for the ultrasonic signals. Then, the existence of damage in a test region R is detected based on the amounts of changes between waveforms of the ultrasonic signals corresponding to the ultrasonic waves U detected by the single ultrasonic sensor 3 or the plural ultrasonic sensors 3 and reference waveforms.

When propagation pathways of ultrasonic waves U differ from each other, waveforms of ultrasonic signals also generally differ from each other. Therefore, it is appropriate to obtain a reference waveform for every position from which an ultrasonic wave U is transmitted and waveforms of ultrasonic signals corresponding to ultrasonic waves U transmitted from plural positions are compared with reference waveforms respectively, from a viewpoint of an improvement in accuracy. That is, it is appropriate to detect the existence of damage in a test region R based on respective amounts of changes between waveforms of ultrasonic signals corresponding to ultrasonic waves U detected by at least one ultrasonic sensor 3 and reference waveforms.

A waveform of an ultrasonic signal which is compared in the waveform comparison part 11F becomes one according to signal processing which is applied. For example, when it is a case where a waveform or waveforms corresponding to a single frequency band or plural frequency bands are obtained by Fourier analysis of a waveform of an ultrasonic signal corresponding to an ultrasonic wave U which was detected by the ultrasonic sensor 3, the existence of damage in a test region R is detected based on each amount of change between the obtained waveform or waveforms corresponding to the single frequency band or the plural frequency bands and a reference waveform or reference waveforms in the corresponding frequency band or the corresponding frequency bands. Moreover, when it is a case where addition averaging processing and noise reduction processing by obtaining a moving average are performed to a waveform of an ultrasonic signal corresponding to an ultrasonic wave U which was detected by the ultrasonic sensor 3, the existence of damage in a test region R is detected based on the amount of change between a waveform which is obtained by the addition averaging processing and the noise reduction processing by obtaining the moving average, and a reference waveform which is obtained by the addition averaging processing and the noise reduction processing by obtaining the moving average.

When only a pair of the ultrasonic transducer 2 and the ultrasonic sensor 3 are placed, it can be determined whether damage exists in a range consisting of a straight line connecting the ultrasonic transducer 2 with the ultrasonic sensor 3, based on an amount of change in waveform of an ultrasonic signal.

Meanwhile, when plural ultrasonic waves U from ultrasonic transducers 2 are detected by at least one ultrasonic sensor 3, it can be determined whether damage exists in a range consisting of straight lines connecting the ultrasonic transducers 2 with the at least one ultrasonic sensor 3. Therefore, a range consisting of a single straight line or plural straight lines in which damage lies can be specified. Thereby, not only the existence of damage but a range of the damage can be detected.

For that reason, when plural ultrasonic waves U from ultrasonic transducers 2 are detected by at least one ultrasonic sensor 3, the waveform comparison part 11F may be made to detect at least one of the existence and an existence range of damage in a test region R, based on amounts of differences between waveforms corresponding to the ultrasonic waves U detected by the at least one ultrasonic sensor 3 and reference waveforms thereof.

When at least one of the existence and an existence range of damage in a test region R was detected, it becomes possible to narrow down the test region R to perform a flaw inspection again. For example, when only a pair of ultrasonic transducer 2 and ultrasonic sensor 3 have been placed, a test can be performed again with shortening a distance between the ultrasonic transducer 2 and the ultrasonic sensor 3. Meanwhile, when ultrasonic waves U from ultrasonic transducers 2 were detected by at least one ultrasonic sensor 3, a test can be performed again by shortening a distance between an ultrasonic transducer 2 and an ultrasonic sensor 3 between which it is determined that damage exists. That is, a narrower test region R can be set for a flaw inspection.

When damage was detected in a test region R and/or when an existence range of the damage was narrowed down well by repeated flaw inspections with narrowing down the test region R, a flaw inspection can be performed by another test method which can detect a position of the damage. For example, a peak of an ultrasonic reflected wave from a test region R can be detected. Then, a position of the damage can be detected based on an acoustic velocity and an elapsed time from transmission timing of the ultrasonic wave to reception timing of the peak of the reflected wave. That is, the existence of damage and a rough position of the damage can be grasped using at least one ultrasonic wave U which transmits a test region R. Then, if damage is detected, a flaw inspection can be performed by an exacter flaw detection method.

Therefore, the waveform comparison part 11F may have a function to detect a position of damage based on a waveform of an ultrasonic reflected wave from a test region R. Alternatively, the waveform comparison part 11F may have a function to detect a position of damage, a size of damage or the like by another ultrasonic flaw detection method.

Note that, it was confirmed through examinations that transmitting an ultrasonic wave, having a comparatively low frequency, of which frequency band was not less than 50 kHz and not more than 150 kHz, to a test region with damage could make an amplitude of a reflected wave, arose by reflecting on the damaged part, large. In particular, it was confirmed that transmitting an ultrasonic wave of which frequency band was not less than 75 kHz and not more than 125 kHz to a test region with damage could generate an ultrasonic reflected wave from the damaged part with a satisfactory SNR. Accordingly, when an ultrasonic wave of which frequency band is not less than 75 kHz and not more than 125 kHz is transmitted to a test region R in which damage exists, it becomes possible to detect an ultrasonic reflected wave with practical accuracy.

Figure 6:
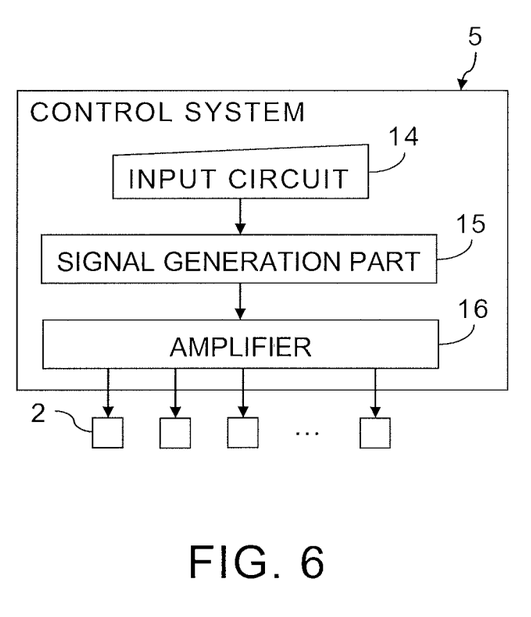
FIG. 6 is a diagram showing an example of detailed configuration of the control system 5 shown in FIG. 1.

FIG. 6 is a diagram showing an example of detailed configuration of the control system 5 shown in FIG. 1.

The control system 5 can be composed of an input circuit 14, a signal generation part 15, and an amplifier 16. Portions, which process digital signals, in the signal generation part 15 can be configured by processing circuitry which executes computer program. Therefore, the portions, which process digital information, of the signal generation part 15 may be integrated with the signal processing circuit 11.

The signal generation part 15 has a function to generate a transmission signal as an electric signal according to direction information input from the input circuit 14, and a function to apply the generated transmission signal to a selected ultrasonic transducer 2 through the amplifier 16. Note that, transmission signals may be output sequentially and automatically to ultrasonic transducers 2 which are output targets of the transmission signals. In that case, in order to automatically set output timing of each transmission signal, synchronous processing between the signal generation part 15 and the signal processing circuit 11 may be performed.

The amplifier 16 is a circuit which amplifies a voltage applied to each ultrasonic transducer 2 so that an ultrasonic wave U having a sufficient intensity can be transmitted from each ultrasonic transducer 2. It was confirmed that an ultrasonic wave U could be actually received with a sufficient SNR using an ultrasonic sensor 3, disposed at a position which was away from a certain ultrasonic transducer 2 by not less than 1000 mm, by applying a transmission signal, which was amplified with the amplifier 16, to the ultrasonic transducer 2.

The ultrasonic test system 1 which has the configuration as described above may be used for an inspection at the time of manufacturing an object W to be tested, and also may be attached to an object W to be tested constantly as a part. In that case, it becomes possible to periodically inspect whether the object W to be tested has a damage or not.

In particular, when an object W to be tested is an aircraft structural object, such as a wing structure or a fuselage, the ultrasonic test system 1 can be attached to the aircraft structural object as a part. In that case, it becomes possible to simply inspect whether damage has arisen in the aircraft structural object using the ultrasonic test system 1 at the time of maintenance and inspection after a flight of the airplane. Moreover, an interval between each ultrasonic transducer 2 and each ultrasonic sensor 3 can be made long. Therefore, the numbers of the ultrasonic transducers 2 and the ultrasonic sensors 3 can be reduced even when an aircraft structural object is large. Consequently, the ultrasonic test system 1 can be attached to an aircraft structural object without an extreme increase in weight of the airplane.

(Operation and Action)

Next, the ultrasonic test method of an object W to be tested, using the ultrasonic test system 1 will be described.

Figure 7:
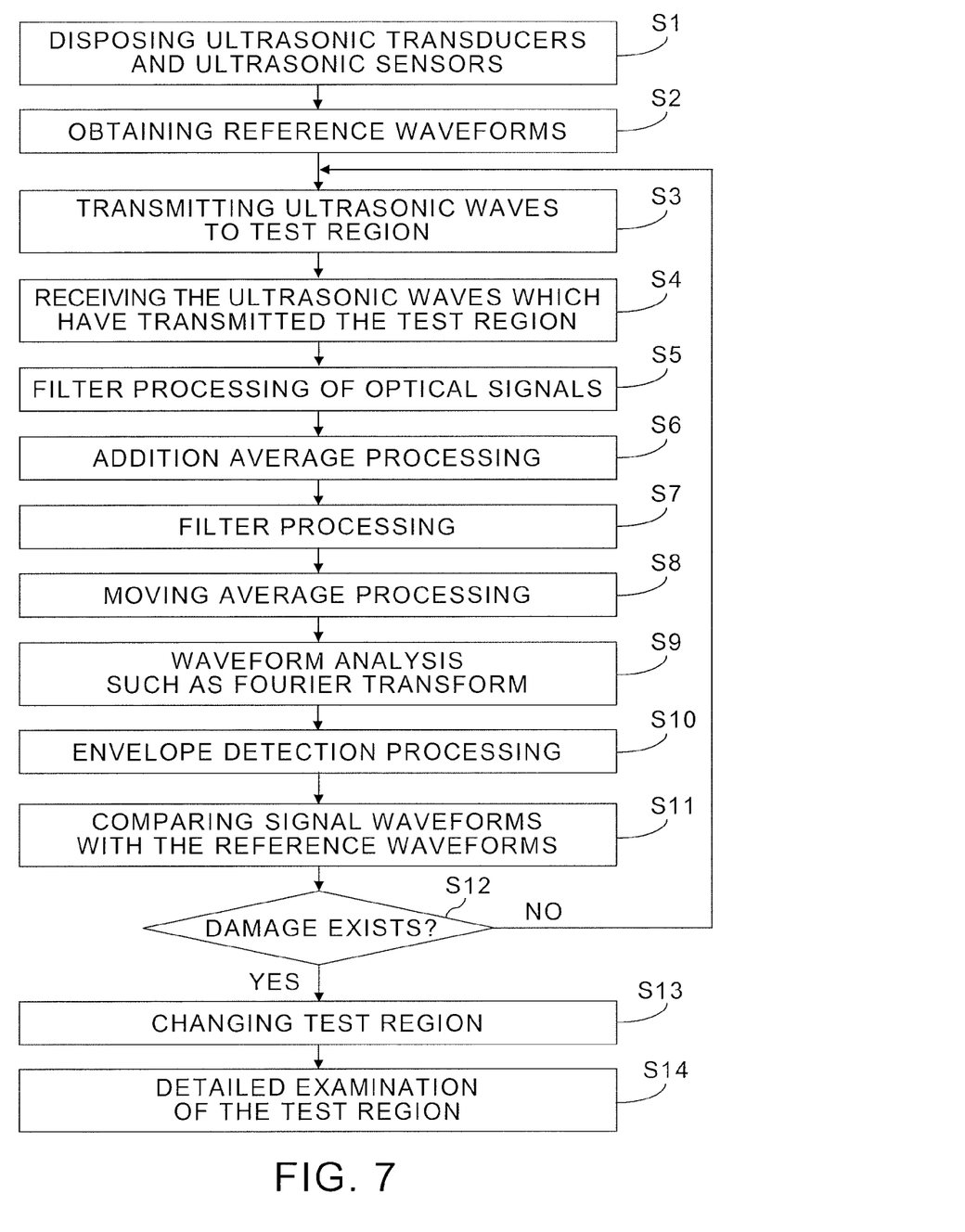
FIG. 7 is a flow chart which shows an example flow in a flaw inspection, for a region to be tested of an object, by the ultrasonic test system shown in FIG. 1.

FIG. 7 is a flow chart which shows an example flow in a flaw inspection, for a region to be tested of an object, by the ultrasonic test system 1 shown in FIG. 1.

Firstly, in Step S1, at least one ultrasonic transducer 2 and at least one ultrasonic sensor 3 are disposed at positions where an ultrasonic wave U can be transmitted towards a test region R of an object W to be tested in which damage does not exist while an ultrasonic wave U which transmitted the test region R is receivable. The distance between each ultrasonic transducer 2 and each ultrasonic sensor 3 can be more than 300 mm. In particular, it is also possible to dispose an ultrasonic transducer 2 and an ultrasonic sensor 3 at positions away from each other by a distance not less than 1000 mm so long as conditions of an ultrasonic wave U, such as frequency and characteristics, and conditions of signal processing of an ultrasonic signal are set preferably.

When the test region R is large, it is preferable to dispose plural ultrasonic transducers 2 and plural ultrasonic sensors 3 so that the test region R may be surrounded by them. Specifically, it is important to dispose plural ultrasonic transducers 2 and plural ultrasonic sensors 3 so that pathways of ultrasonic waves U which pass the test region R may become dense enough. In addition, it is also effective to dispose two pairs of ultrasonic transducers 2 and ultrasonic sensors 3 in the opposite directions to each other, from a viewpoint of making pathways of ultrasonic waves U dense.

Moreover, it is desirable to dispose each ultrasonic transducer 2 and each ultrasonic sensor 3 on appropriate positions according to a structure of an object W to be tested. For example, when an object W to be tested has a structure in which at least one elongated structure W2 is attached on a platy part W1, such as a wing structure or a fuselage of an aircraft in which stringers are attached on a panel, it is preferable to dispose at least one pair of an ultrasonic transducer 2 and an ultrasonic sensor 3 in each of the both side of the at least one elongated structure W2 as exemplified in FIG. 1 and FIG. 2. When the ultrasonic transducers 2 and the ultrasonic sensors 3 are disposed as described above, it becomes possible to detect an ultrasonic wave U, having a sufficient intensity, in each area segmented with the elongated structure W2, by each ultrasonic sensor 3 even when an ultrasonic wave U which transmitted the elongated structure W2 has an insufficient intensity.

Furthermore, when an object W to be tested has a structure in which plural elongated structures W2 are attached on a platy part W1, it is preferable to dispose at least one pair of an ultrasonic transducer 2 and an ultrasonic sensor 3 between at least two adjacent elongated structures W2 as exemplified in FIG. 1 and FIG. 2. When the ultrasonic transducers 2 and the ultrasonic sensors 3 are disposed in such a way, an ultrasonic wave U propagates from an ultrasonic transducer 2 toward an ultrasonic sensor 3 while the ultrasonic wave U is reflected between adjacent elongated structures W2, thereby an amount of attenuation of the ultrasonic wave U can be reduced.

Moreover, it is preferable to use an optical fiber sensor, such as an FBG sensor 3A or a PS-FBG sensor, as each ultrasonic sensor 3 from a viewpoint of detecting an ultrasonic wave U with a satisfactory SNR and high sensitivity. Accordingly, a case where each ultrasonic sensor 3 is an FBG sensor 3A will be explained here.

Next, in Step S2, a reference waveform of an ultrasonic signal corresponding to an ultrasonic wave U which transmitted the test region R in which damage does not exit is obtained. For that purpose, an ultrasonic wave U of which frequency is not less than 50 kHz and not more than 500 kHz, more desirably, not less than 50 kHz and not more than 150 kHz is transmitted from an ultrasonic transducer 2 to the test region R of the object W to be tested where damage does not exist. Moreover, preferable conditions are that the ultrasonic wave U is a Lamb wave having directivity and advancing in a sector form, from a viewpoint of detecting an ultrasonic wave U which propagated the large test region R with a satisfactory SNR.

When plural ultrasonic transducers 2 are placed, ultrasonic waves U are transmitted sequentially from the ultrasonic transducers 2. Then, the ultrasonic waves U which passed the test region R are detected by at least one ultrasonic sensor 3. When plural ultrasonic sensors 3 are placed, ultrasonic wave U or ultrasonic waves U transmitted from a single ultrasonic transducer 2 or plural ultrasonic transducers 2 are detected by each detectable ultrasonic sensor 3.

The ultrasonic wave U or ultrasonic waves U detected by the single ultrasonic sensor 3 or the plural ultrasonic sensors 3 are output to the damage detection part 4. In the damage detection part 4, a waveform of an ultrasonic signal corresponding to each ultrasonic wave U is detected with necessary signal processing. Examples of preferable signal processing to be performed prior to detect a waveform of an ultrasonic signal include filter processing of an optical signal by which a vibration in wavelength of the optical signal is converted into a vibration in intensity, addition averaging processing, filtering processing for noise reduction, moving averaging processing, waveform analysis processing, such as Fourier transform, and envelope detection processing.

The waveform of the detected ultrasonic signal is recorded on the storage 13 of the damage detection part 4 as a reference waveform. When plural ultrasonic signals whose waveforms are different from each other have been detected, the waveforms are recorded on the storage 13 of the damage detection part 4 as reference waveforms respectively. When the reference waveform for every propagation pathway of an ultrasonic wave U has been recorded on the storage 13, it becomes possible to start a flaw inspection of the object W to be tested.

For example, when a flaw inspection is performed at the time of a mass production of the object W to be tested, the flaw inspection can be started one by one for a number of the objects W. Meanwhile, when the ultrasonic test system 1 is attached to the object W to be tested as a part or a temporary attachment, a flaw inspection can be started at a desired time, such as each time of periodic inspection.

When a flaw inspection is started, in Step S3, an ultrasonic wave U is transmitted towards the test region R of the object W to be tested by at least one ultrasonic transducer 2 under conditions similar to the conditions for obtaining the reference waveform. When plural ultrasonic transducers 2 have been placed on the object W to be tested, ultrasonic waves U are transmitted sequentially from the ultrasonic transducers 2.

Then, in Step S4, the ultrasonic wave U which passed the test region R can be detected by at least one ultrasonic sensor 3 placed on a position away from the ultrasonic transducer 2 by a distance longer than 300 mm. When ultrasonic waves U were transmitted towards the test region R from different positions by the ultrasonic transducers 2, the ultrasonic waves U, which passed the test region R, from the ultrasonic transducers 2 are detected by at least one ultrasonic sensor 3. Each ultrasonic wave U detected by the FBG sensor 3A used as the ultrasonic sensor 3 is output to the damage detection part 4 as an optical signal in which a wavelength vibrates according to a vibration in intensity of the ultrasonic wave U.

Next, in Step S5, each optical signal output from the FBG sensor 3A enters the optical filter 8 through the optical circulator 7. Then, each optical signal in which the wavelength vibrates is converted into an optical signal in which intensity vibrates with a larger amplitude. Thereby, each optical signal is amplified substantially. Each optical signal output from the optical filter 8 is converted into an electric signal in the photoelectric converter 9, and subsequently the electric signal is digitized in the A/D converter 10. Each digitized electric signal is output to the signal processing circuit 11 as an ultrasonic detection signal.

Next, in Step S6, addition averaging processing of the ultrasonic detection signals is performed by the addition averaging processing part 11A. Next, in Step S7, filter processing of each ultrasonic detection signal is performed using an LPF and/or an HPF by the filter processing part 11B. Next, in Step S8, moving averaging processing is performed as smoothing processing to reduce noises of each ultrasonic detection signal by the moving averaging processing part 11C. Next, in Step S9, wave analysis processing, such as Fourier transform processing, of each ultrasonic detection signal, is performed by the waveform analysis part 11D. Next, in Step S10, envelope detection processing of each ultrasonic detection signal is performed by the envelope detection processing part 11E.

By the above mentioned signal processing of each optical signal and each electric signal, a waveform of ultrasonic signal or waveforms of ultrasonic signals from which change from the reference waveform or changes from the reference waveforms can be detected in high sensitivity with an extremely satisfactory SNR can be obtained. Note that, a part of the signal processing sets may be omitted according to accuracy required for a flaw inspection. On the contrary, other signal processing may be added according to accuracy required for a flaw inspection. Moreover, an order of the signal processing sets may be changed to a possible extent. In particular, it is important to perform at least one of Fourier analysis and noise reduction processing by obtaining a moving average, as signal processing of an electric signal, from a viewpoint of detecting a change in waveform with high sensitivity.

Next, in Step S11, each waveform of ultrasonic signal after the signal processing is compared with the reference waveform in the waveform comparison part 11F. Then, based on the amount of change between the waveform of the ultrasonic signal corresponding to the ultrasonic wave U detected by the ultrasonic sensor 3 and the reference waveform, the existence of damage in the test region R is detected. Specifically, when the amount of change between the waveform of the ultrasonic signal corresponding to the ultrasonic wave U detected by the ultrasonic sensor 3 and the reference waveform exceeds a predetermined reference value or is not less than a predetermined reference value, it is determined that damage exists on the propagation pathway of the ultrasonic wave U.

When the waveforms of the ultrasonic signals corresponding to the ultrasonic waves U transmitted from the plural ultrasonic transducers 2 have been obtained, the waveforms of the ultrasonic signals are compared with the corresponding reference waveforms respectively. Therefore, it can be determined whether damage exists on each of the propagation pathways of the ultrasonic waves U. As a result, an existence range of the damage can be detected by distinguishing each propagation pathway of ultrasonic wave U with the damage from each propagation pathway of ultrasonic wave U without the damage.

When waveforms corresponding to frequency bands have been obtained by Fourier analysis of the waveform of the ultrasonic wave U detected by the ultrasonic sensor 3, the existence of damage in the test region R can be detected with higher precision, based on amounts of changes between the obtained waveforms corresponding to the frequency bands and corresponding reference waveforms in the frequency bands. Alternatively, when a single waveform corresponding to a specific frequency band has been obtained by Fourier analysis of the waveform of the ultrasonic wave U detected by the ultrasonic sensor 3, the existence of damage in the test region R can be detected with higher precision based on an amount of change between the obtained single waveform and a corresponding reference waveform.

Next, in Step S12, it is determined whether damage was detected in the test region R. This judgment may be performed by a user. When damage was not detected in the test region R, a similar flaw inspection from Step S3 can be performed again at an appropriate time. For example, when objects W to be inspected are inspected one by one, a flaw inspection can be restarted with targeting the next object W to be inspected. Meanwhile, when the ultrasonic test system 1 is attached to the object W to be tested as a part or a temporary attachment, a flaw inspection can be restarted at a desired time, such as a time of a next periodic inspection or the like.

When damage was detected in the test region R, in Step S13, a new test region which includes the detected damage and is narrower than the test region R is set. A flaw inspection for the new test region may be performed using the ultrasonic test system 1, or may be performed using another ultrasonic test system or a test system other than the ultrasonic test system.

As the case of inspecting objects W to be inspected one by one using the same ultrasonic test system 1, when each ultrasonic transducer 2 and each ultrasonic sensor 3 can be removed easily from an object W to be tested, the new test region can be set by changing positions of at least one ultrasonic transducer 2 and/or at least one ultrasonic sensor 3. Meanwhile, when a flaw inspection in the new test region is performed using another test system, a necessary sensor or sensors are disposed so that sensing the damage can be performed for the new test region.

Next, in Step S14, a nondestructive test of the damage is performed for the new test region. When a nondestructive test of the damage for the new test region is performed using the same ultrasonic test system 1, a test as described above may be performed to detect the existence of damage based on change of a waveform of an ultrasonic wave U, which transmits the new test region, from a reference waveform. In that case, a test region can be gradually narrowed by repeating ultrasonic flaw inspections.

Meanwhile, another voluntary nondestructive test can also be performed. For example, when a test region of the damage has been narrowed sufficiently as the case where a width of the test region of the damage has been set to not more than 100 mm, a test which detects a position of the damage based on an ultrasonic reflected wave from the new test region may be performed as a nondestructive test of the damage in the new test region. Specifically, based on transmitting timing of an ultrasonic wave, an arrival time of a peak of a reflected wave which is reflected in the new test region and an acoustic velocity, the position of the damage can be detected.

As described above, the ultrasonic test system 1 and the ultrasonic test method can detect whether damage has arisen even when a test region R is a meter order class, by transmitting an ultrasonic wave U to the test region R under more effective conditions from viewpoints of an improvement in SNR and an increase in sensitivity, and by effective signal processing of an optical signal and an electric signal corresponding to an ultrasonic wave U detected by an ultrasonic sensor 3.

(Effect)

According to the ultrasonic test system 1 and the ultrasonic test method, the existence of damage can be detected for a test region R, which is larger than the conventional area, with high precision using a small number of ultrasonic sensors 3. In other words, when the existence of damage is inspected for a large test region R, it can be avoided that the numbers of ultrasonic transducers 2 and ultrasonic sensors 3 increase extremely.

Conventionally, detecting an ultrasonic reflected wave reflected in a damaged area has been performed as the method of detecting a position or a size of the damage with high precision. However, in order to detect a position or a size of damage with high precision, it is necessary to detect an ultrasonic reflected wave from a damaged area. In this case, only a damage which exists at a short distance in the traveling direction of an ultrasonic wave can be detected. That is, when a position or a size of damage try to be detected with high precision, it becomes difficult to detect the damage in a wide area.

Meanwhile, the ultrasonic test system 1 and the ultrasonic teat method do not detect a position and a size of damage with high precision, but simply detect whether damage exists in a test region R. Therefore, it is possible to perform a flaw inspection in a very wide range. Moreover, a detailed inspection for detecting a position and a size of damage has only to be performed when damage was detected. As a result, a flaw inspection of an object W to be tested can be performed without using a complicated ultrasonic test system for detecting a position or a size of damage all the time. Therefore, a time, labor, and cost which the whole inspection of an object W to be tested requires can be reduced.

Moreover, when the ultrasonic test system 1 is attached as a part of an aircraft structural object, it can be diagnosed easily whether damage has occurred in the aircraft structural object to which the ultrasonic test system 1 has been attached, at the time of a periodic check of the aircraft. Moreover, extreme increases in the numbers of ultrasonic transducers 2 and ultrasonic sensors 3 can be avoided, and therefore, an extreme increase in weight of an aircraft can be also avoided.

While certain implementations have been described, these implementations have been presented by way of example only, and are not intended to limit the scope of the invention. Indeed, the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms or modifications as would fall within the scope and spirit of the invention.

What is claimed is:

1. An ultrasonic test system comprising:
ultrasonic transducers configured to transmit Lamb waves toward at least one test region of an object to be tested, the object comprising a material that is at least one of a metal or a composite, the object having a plate part and an elongated structural object disposed on the plate part, the ultrasonic transducers being disposed at a first side and a second side of the elongated structural object, the Lamb waves each having a frequency not less than 50 kHz and not more than 150 kHz;
optical fiber sensors configured to detect Lamb waves that have passed through the at least one test region and output detection signals in the form of oscillations in light wavelengths, the optical fiber sensors being disposed at the first side and the second side of the elongated structural object;
an optical filter configured to amplify the detection signals output from the optical fiber sensors to have larger amplitudes by oscillation of light intensities; and
a damage detection circuit configured to obtain waveforms of the Lamb waves, with each obtained waveform of a Lamb wave corresponding to at least one frequency band, the waveforms of the Lamb waves being obtained by signal processing of the detection signals amplified by the optical filter, the signal processing comprising addition averaging processing, noise reduction processing, calculating moving averages, and waveform analysis by one of a Fourier transform or a wavelet transform,
wherein the damage detection circuit is further configured to determine whether there is damage in the at least one test region based on respective differences between waveforms of the Lamb waves and reference waveforms,
wherein at least one of the ultrasonic transducers and at least one of the optical fiber sensors are disposed at respective positions spaced apart from one another by an interval of not less than 1000 mm.

2. The ultrasonic test system according to claim 1, wherein
the ultrasonic transducers are configured to transmit Lamb waves from different positions toward the at least one test region,
at least one optical fiber sensor is configured to detect each of the Lamb waves that are transmitted from the ultrasonic transducers and passed through the at least one test region; and
the damage detection circuit is configured to determine a scope of the damage in the at least one test region based on respective differences between waveforms of the Lamb waves detected by the at least one optical fiber sensor and reference waveforms.

3. The ultrasonic test system according to claim 1, wherein the ultrasonic transducers are configured to transmit each of the Lamb waves with directivity and to propagate in a sector form.

4. An aircraft structural object comprising the ultrasonic test system according to claim 1.

5. The aircraft structural object according to claim 4, wherein
a first oft of an ultrasonic transducer and an optical fiber sensor is disposed opposite a second pair of an ultrasonic transducer and an optical fiber sensor, the opposing pairs of ultrasonic transducers and optical fiber sensors being positioned between at least two adjacent elongated structural objects disposed on the plate part.

6. An ultrasonic test system comprising
ultrasonic transducers configured to transmit Lamb, toward at least one test region of an object to be tested, the object having a plate part and an elongated structural object disposed on the plate part, the ultrasonic transducers being disposed at a first side and a second side of the elongated structural object, the Lamb waves each having a frequency of not less than 50 kHz and not more than 150 kHz;
optical fiber sensors configured to detect Lamb waves that have passed through the at least one test region and output detection signals in the form of oscillations in light wavelengths, the optical fiber sensor being disposed at the first side and the second side of the elongated structural object;
an optical filter configured to amplify the detection signals output from the optical fiber sensors to have larger amplitudes by oscillation of light intensities; and
a damage detection circuit configured to obtain waveforms of the Lamb waves, with each obtained waveform of a Lamb wave corresponding to at least one frequency band, the waveforms of the Lamb waves being obtained by signal processing of the detection signals amplified by the optical filter, the signal processing comprising addition average processing, noise reduction processing, calculating moving averages, and waveform analysis by one of a Fourier transform or a wavelet transform,
wherein the damage detection circuit is further configured to determine whether there is damage in the at least one test region based on respective differences between waveforms of the Lamb waves and reference waveforms, and
wherein a first pair of an ultrasonic transducer and an optical fiber sensor is disposed opposite a second pair of an ultrasonic transducer and an optical fiber sensor on both the first side and the second side of the elongated structural object, the opposing pairs of ultrasonic transducers and optical fiber sensors being configured to transmit Lamb waves bidirectionally in at least the respective sides of the elongated structural object.

7. An aircraft structural object comprising the ultrasonic test system according to claim 6.

8. The ultrasonic test system according to claim 6, wherein
the ultrasonic transducers are configured to transmit Lamb waves from different positions toward the at least one test region,
at least one optical fiber sensor is configured to detect each of the Lamb waves that are transmitted from the ultrasonic transducers and passed through the at least one test region; and
the damage detection circuit is configured to further detect a scope of a detected damage in the at least one test region based on respective differences between waveforms of the Lamb waves detected by the at least one optical fiber sensor and reference waveforms.

9. An ultrasonic test method comprising:
transmitting Lamb waves toward a test region of an object to be tested, the object comprising a material that is at least one of a metal or a composite, the object having a plate pan and an elongated structural object disposed on the plate part, the Lamb waves being transmitted by ultrasonic transducers disposed at a first side and a second side of the elongated structural object, a frequency of each Lamb wave being not less than 50 kHz and not more than 150 kHz;
detecting the Lamb waves, having passed through the test region, by optical fiber sensors disposed at the first side and the second side of the elongated structural object;
outputting detection signals based on the detected Lamb waves, the detection signals being output from the optical fiber sensors in the form of oscillations in light wavelengths;
amplifying the detection signals by an optical filter to have larger amplitudes by oscillations of light intensities;
signal processing amplified detection signals to obtain waveforms the Lamb waves, with each obtained waveform of a Lamb wave corresponding to at least one frequency band, the signal processing comprising addition averaging processing, noise reduction processing, calculating moving averages, and waveform analysis by one of a Fourier transform or a wavelet transform; and
determining whether there is damage in the test region based on respective differences between waveforms of the Lamb waves and reference waveforms,
wherein the Lamb waves are transmitted from ultrasonic transducers and detected by optical fiber sensors, with at least one Lamb wave being transmitted by an ultrasonic transducer and detected by an optical fiber sensor that are spaced apart from one another by an interval of not less than 1000 mm.

10. The ultrasonic test method according to claim 9, further comprising:
when it is determined that there is damage in the test region, reset the test region to a narrowed test region that includes the damage and perform a nondestructive test of the damage in the narrowed test region.

11. The ultrasonic test method according to claim 10,
wherein a test to detect a position of the damage based on a reflected wave of a Lamb wave is performed as the nondestructive test of the damage in the narrowed test region.

12. The ultrasonic test method according to claim 9,
wherein a first pair of an ultrasonic transducer and an optical fiber sensor is disposed opposite a second pair of an ultrasonic transducer and an optical fiber sensor on both the first side and the second side of the elongated structural object, the opposing pairs of ultrasonic transducers and optical fiber sensors being configured to transmit Lamb waves bidirectionally in at least the respective sides of the elongated structural object.

13. An ultrasonic test method comprising:
transmitting Lamb waves toward a test region of an object to be tested, the object having a plate part and an elongated structural object disposed on the plate part, the Lamb waves being transmitted by ultrasonic transducers disposed at a first side and a second side of the elongated structural object, a frequency of each of the Lamb waves being not less than 50 kHz and not more than 150 kHz;
detecting the Lamb waves, having passed through the test region, by optical fiber sensors disposed at the first side and the second side of the elongated structural object;
outputting detection signals based on the detected Lamb waves, the signals being output from the optical fiber sensors in the form of oscillations in light wavelengths;
amplifying the detection signals by an optical filter to have larger amplitudes by oscillations of light intensities;
signal processing amplified detection signals to obtain waveforms of the Lamb waves, with each obtained waveform of a Lamb wave corresponding to at least one frequency band, the signal processing comprising addition averaging processing, noise reduction processing, calculating moving averages, and waveform analysis by one of a Fourier transform or a wavelet transform; and
determining whether there is damage in the test region based on respective differences between waveforms of the Lamb waves and reference waveforms,
wherein a first pair of an ultrasonic transducer and an optical fiber sensor is disposed opposite a second pair of an ultrasonic transducer and an optical fiber sensor on both the first side and the second side of the elongated structural object, the opposing pairs of ultrasonic transducers and optical fiber sensors being configured to transmit Lamb waves bidirectionally in at least the respective sides of the elongated structural object.

* * * * *